(12) United States Patent
Buettner et al.

(10) Patent No.: US 6,951,888 B2
(45) Date of Patent: Oct. 4, 2005

(54) BETAMIMETICS WITH A PROLONGED DURATION OF ACTIVITY, PROCESSES FOR PREPARING THEM, AND THEIR USE AS PHARMACEUTICAL COMPOSITIONS

(75) Inventors: Frank Buettner, Ummendorf (DE); Ingo Konetzki, Warthausen (DE); Kurt Schromm, Ingelheim (DE); Hermann Schollenberger, Ingelheim (DE); Sabine Pestel, Biberach (DE); Andreas Schnapp, Biberach (DE); Thierry Bouyssou, Mietingen (DE); Claudia Heine, Biberach (DE)

(73) Assignee: Boehringer Ingelheim Pharma Gmbh & Co. KG, Ingelheim (DE)

( * ) Notice: Subject to any disclaimer, the term of this patent is extended or adjusted under 35 U.S.C. 154(b) by 0 days.

(21) Appl. No.: 10/666,068

(22) Filed: Sep. 19, 2003

(65) Prior Publication Data

US 2004/0122108 A1 Jun. 24, 2004

Related U.S. Application Data

(60) Provisional application No. 60/432,499, filed on Dec. 11, 2002.

(30) Foreign Application Priority Data

Oct. 4, 2002 (DE) ......................................... 102 46 374

(51) Int. Cl.⁷ ..................... A61K 31/047; C07C 215/58
(52) U.S. Cl. ..................... 514/563; 564/360; 564/361; 564/362
(58) Field of Search .................... 514/653; 564/360–362

(56) References Cited

U.S. PATENT DOCUMENTS 3,657,244 A  4/1972  Mentrup et al.
5,223,614 A  6/1993  Schromm et al.
2002/0022625 A1  2/2002  Walland et al.

FOREIGN PATENT DOCUMENTS

DE   1 543 374       4/1972
EP   0 321 864 A2    6/1989
WO   WO 01/83462 A1  11/2001

OTHER PUBLICATIONS

Database CAPLUS on STN, Acc. No. 1969:523933, MENTRUP et al, ZA 6802425 (Nov. 8, 1968) (abstract).*

* cited by examiner

*Primary Examiner*—Brian Davis
(74) *Attorney, Agent, or Firm*—Michael Morris; Mary-Ellen M. Devlin; Andrea D. Small

(57) ABSTRACT

A compound of formula 1

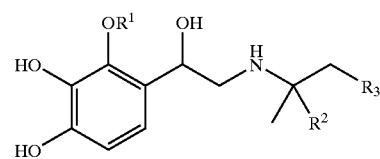

wherein: $R^1$ is $C_1$–$C_4$-alkyl; $R^2$ is $C_1$–$C_4$-alkyl; and $R^3$ is $C_1$–$C_4$-alkyl or phenyl, each optionally mono- or polysubstituted, or $R^2$ and $R^3$ together are —$CH_2$—$CH_2$— or —$CH_2$—$CH_2$—$CH_2$—, or the corresponding acid addition salt with a pharmacologically acceptable acid, processes for preparing such compounds, pharmaceutical compositions containing such compounds, and their use in the treatment of inflammatory and obstructive respiratory diseases.

31 Claims, No Drawings

BETAMIMETICS WITH A PROLONGED DURATION OF ACTIVITY, PROCESSES FOR PREPARING THEM, AND THEIR USE AS PHARMACEUTICAL COMPOSITIONS

RELATED APPLICATIONS

This application claims benefit of U.S. Ser. No. 60/432,499, filed Dec. 11, 2002, and claims priority to German Application No. 102 46 374.3, filed Oct. 4, 2002, each of which is hereby incorporated by reference in its entirety.

FIELD OF THE INVENTION

The present invention relates to compounds of general formula 1

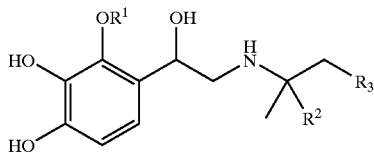

wherein the groups $R^1$, $R^2$, and $R^3$ may have the meanings given in the claims and in the specification, processes for preparing them, and their use as pharmaceutical compositions, particularly for the treatment of inflammatory and obstructive respiratory complaints.

BACKGROUND OF THE INVENTION

Betamimetics (β-adrenergic substances) are known from the prior art. They may be used to good effect in a variety of therapeutic fields.

For drug treatment of diseases, it is often desirable to prepare medicaments with a longer duration of activity. As a rule, this ensures that the concentration of the active substance in the body needed to achieve the therapeutic effect is guaranteed for a longer period without the need to readminister the drug at frequent intervals. Moreover, giving an active substance at longer time intervals contributes to the well-being of the patient to a high degree. Another major advantage of drugs with a longer duration of activity is apparent in the case of diseases or illnesses the symptoms of which only appear in the second half of the night. A single application of a drug with a longer duration of activity before going to sleep would make things much simpler for the patient and represent an improvement in the quality of life. It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide betamimetics which are characterized by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day. A further objective of the invention is to prepare new betamimetics which, by virtue of their long-lasting effect, can be used to prepare a drug for administration once a day for the treatment of inflammatory or obstructive respiratory complaints.

In addition to the above objectives, the present invention also sets out to provide betamimetics which are not only exceptionally potent but are also characterized by a high degree of selectivity with respect to the $β_2$-adrenoreceptor.

DETAILED DESCRIPTION OF THE INVENTION

Surprisingly it has been found that the abovementioned problems are solved by compounds of general formula 1.

Accordingly, the present invention relates to compounds of general formula 1

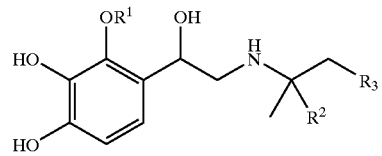

wherein:
$R^1$ denotes $C_1$–$C_4$-alkyl;
$R^2$ denotes $C_1$–$C_4$-alkyl; and
$R^3$ denotes $C_1$–$C_4$-alkyl or phenyl, which may optionally be mono- or polysubstituted, or $R^2$ and $R^3$ together denote a double-bonded group selected from —$CH_2$—$CH_2$— and —$CH_2$—$CH_2$—$CH_2$—.

Preferred are compounds of formula 1, wherein:
$R^1$ denotes $C_1$–$C_4$-alkyl;
$R^2$ denotes $C_1$–$C_4$-alkyl; and
$R^3$ denotes $C_1$–$C_4$-alkyl or phenyl, which may optionally be mono-, di-, tri-, or tetrasubstituted by one or more groups selected from $C_1$–$C_3$-alkyl, —$CF_3$, methoxy, ethoxy, hydroxy, fluorine, chlorine, bromine, —$OCF_3$, —$CHF_2$, —$NHCOCH_3$, and —$NHSO_2CH_3$, or $R^2$ and $R^3$ together denote a double-bonded group selected from —$CH_2$—$CH_2$— and —$CH_2$—$CH_2$—$CH_2$—.

Also preferred are compounds of general formula 1, wherein:
$R^1$ denotes $C_1$–$C_4$-alkyl, preferably methyl;
$R^2$ denotes $C_1$–$C_4$-alkyl; and
$R^3$ denotes $C_1$–$C_4$-alkyl or phenyl, which may optionally be mono-, di-, tri-, or tetrasubstituted by one or more groups selected from methyl, ethyl, —$CF_3$, methoxy, ethoxy, and hydroxy, or $R^2$ and $R^3$ together denote a double-bonded group selected from —$CH_2$—$CH_2$— and —$CH_2$—$CH_2$—.

Also preferred are compounds of general formula 1, wherein:
$R^1$ denotes $C_1$–$C_4$-alkyl, preferably methyl;
$R^2$ denotes $C_1$–$C_4$-alkyl, preferably methyl; and
$R^3$ denotes $C_1$–$C_4$-alkyl, preferably methyl, or phenyl, which may optionally be mono-, di-, tri-, or tetrasubstituted by one or more groups selected from methyl, —$CF_3$, methoxy, and hydroxy, or $R^2$ and $R^3$ together denote the double-bonded group —$CH_2$—$CH_2$—.

Preferred compounds of general formula 1 according to the invention are those wherein:
$R^1$ denotes methyl or ethyl, preferably methyl;
$R^2$ denotes methyl; and
$R^3$ denotes methyl, ethyl or phenyl, which may optionally be mono-, di-, tri-, or tetrasubstituted by one or more groups selected from methyl, —$CF_3$, methoxy, and hydroxy, or $R^2$ and $R^3$ together denote the double-bonded group —$CH_2$—$CH_2$—.

Particularly preferred are compounds of general formula 1 wherein:
$R^1$ denotes methyl;
$R^2$ denotes methyl; and $R^3$ denotes methyl or phenyl, which may optionally be mono-, di-, or trisubstituted by one or more groups selected from methyl, ethyl, and hydroxy, or $R^2$ and $R^3$ together denote the double-bonded group —CH$_2$—CH$_2$—.

Also preferred according to the invention are compounds of general formula 1, wherein:
$R^1$ denotes methyl;
$R^2$ denotes methyl; and
$R^3$ denotes methyl or phenyl, or $R^2$ and $R^3$ together denote the double-bonded group —CH$_2$—CH$_2$—.

Of exceptional importance according to the invention are, for example, the following compounds of formula 1:

- 4-[2-(1,1-dimethylpropylamino)-1-hydroxyethyl]-3-methoxybenzene-1,2-diol;
- 4-[1-hydroxy-2-(1-methylcyclopentylamino)ethyl]-3-methoxybenzene-1,2-diol;
- 4-{2-[1,1-dimethyl-2-(2,4,6-trimethylphenyl)ethylamino]-1-hydroxyethyl}-3-methoxybenzen 1,2-diol;
- 4-{2-[1,1-dimethyl-2-phenyl)ethylamino]-1-hydroxyethyl}-3-methoxybenzene-1,2-diol;
- 4-{2-[1,1-dimethyl-2-(2,3,5,6-tetramethylphenyl)ethylamino]-1-hydroxyethyl}-3-methoxybenzene-1,2-diol; and
- 4-[2-(1,1-dimethyl-2-o-tolylethylamino)-1-hydroxyethyl]-3-methoxybenzene-1,2-diol.

The invention relates to the compounds of formula 1, optionally in the form of the individual optical isomers, mixtures of the individual enantiomers or racemates, in the form of the free bases or the corresponding acid addition salts with pharmacologically acceptable acids.

The compounds of general formula 1 according to the invention may optionally occur in the form of their individual optical isomers, mixtures of the individual enantiomers or racemates and may be separated into the pure forms using methods known from the literature. If the compounds are used in enantiomerically pure form, the R-enantiomers are preferred.

By acid addition salts are meant the salts formed with pharmacologically acceptable acids selected from among hydrochloric acid, hydrobromic acid, hydroiodic acid, sulfuric acid, phosphoric acid, methanesulfonic acid, nitric acid, maleic acid, acetic acid, benzoic acid, citric acid, fumaric acid, tartaric acid, oxalic acid, succinic acid, and p-toluenesulfonic acid, preferably hydrochloric acid, hydrobromic acid, sulfuric acid, phosphoric acid, fumaric acid, and methanesulfonic acid.

Unless otherwise stated, the alkyl groups are straight-chained or branched alkyl groups having 1 to 4 carbon atoms. The following are mentioned by way of example: methyl, ethyl, propyl, or butyl. In some cases, the abbreviations Me, Et, Prop, or Bu are used to denote the groups methyl, ethyl, propyl, or butyl. Unless otherwise stated, the definitions propyl and butyl include all the possible isomeric forms of the groups in question. Thus, for example, propyl includes n-propyl and isopropyl, butyl includes isobutyl, sec-butyl, and tert-butyl, etc.

Of the abovementioned acid addition salts, the salts of hydrochloric acid, methanesulfonic acid, benzoic acid, and acetic acid are particularly preferred according to the invention.

The compounds according to the invention may be prepared analogously to the methods already known in the art. Suitable methods of preparation are known, for example, from U.S. Pat. No. 3,657,244, which is hereby incorporated by reference.

The examples of synthesis described below serve to illustrate the present invention more fully. They are intended only as examples of procedure to illustrate the invention without restricting it to the subject matter described hereinafter.

EXAMPLE 1

4-[2-(1,1-dimethylpropylamino)-1-hydroxyethyl]-3-methoxybenzene-1,2-diol

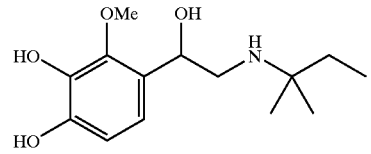

(a) 2-(1,1-dimethylpropylamino)-1-(4-methoxy-2,2-diphenylbenzo[1,3]dioxol-5-yl)ethanone 42.5 g of α-bromo-2-methoxy-3,4-diphenylmethylenedioxyacetophenone (obtainable according to U.S. Pat. No. 3,657,244) is refluxed with 30 g of 1,1-dimethylpropylamine in 150 mL of ethanol for 3 hours with stirring. The solvent is distilled off under reduced pressure and the residue is combined with diethyl ether and extracted twice with water. After the solvent has been distilled off under reduced pressure, the residue remaining is dissolved in ethyl acetate and acidified with ethereal hydrochloric acid. The precipitated crystals are suction filtered and washed with ethyl acetate and diethyl ether. Yield: 26 g (56%, hydrochloride); melting point: 174° C.–176° C.

(b) 1-(3,4-dihydroxy-2-methoxyphenyl)-2-(1,1-dimethylpropylamino)ethanone 25 g of 2-(1,1-dimethylpropylamino)-1-(4-methoxy-2,2-diphenylbenzo[1,3]dioxol-5-yl) ethanone is refluxed with 50 mL of 15% methanolic hydrochloric acid for 2 hours with stirring. The solvent is distilled off under reduced pressure and the residue is dissolved in acetonitrile and combined with ethyl acetate. The precipitated crystals are suction filtered and washed with acetonitrile and diethyl ether. Yield: 15 g (92%) of the compound as the hydrochloride.

For further purification, the free base may be released from the hydrochloride under the usual conditions, then suspended in methanol, combined with an equimolar amount of benzoic acid, and heated. The crystals thus obtained are suction filtered and washed with diethyl ether. Melting point: 151° C.–154° C. (benzoate).

(c) 4-[2-(1,1-dimethylpropylamino)-1-hydroxyethyl]-3-methoxybenzene-1,2-diol 6.5 g of 1-(3,4-dihydroxy-2-methoxyphenyl)-2-(1,1-dimethylpropylamino)ethanone are hydrogenated with 0.1 g of platinum oxide as catalyst in 125 mL of methanol. The catalyst is suction filtered and the solvent is distilled off under reduced pressure. The residue is dissolved in ethyl acetate, the precipitated crystals are suction filtered and washed with ethyl acetate and diethyl ether. Yield: 5.5 g (85%; benzoate); melting point: 172° C.–174° C.

EXAMPLE 2

4-[1-hydroxy-2-(1-methylcyclopentylamino)ethyl]-3-methoxybenzene-1,2-diol

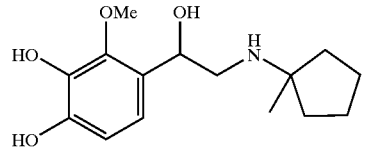

(a) 1-methylcyclopentylamine 66.5 g of sodium cyanide is dissolved in 150 mL glacial acetic acid. A solution of 300 mL of sulfuric acid and 150 mL of glacial acetic acid is added dropwise at 5° C.–10° C. to the sodium cyanide solution. 126 g of 1-methylcyclopentanol are added to this mixture. The mixture obtained is left to stand overnight. Then 210 mL of water and, while cooling with ice, 770 g of sodium hydroxide solution in 1.5 L of water are added thereto. The mixture is refluxed for 4 hours and the amine is isolated by steam distillation. The distillate is acidified with concentrated hydrochloric acid, extracted with diethyl ether, and then made alkaline with 50% sodium hydroxide solution. The residue is then fractionally distilled ($bp_{760\,mm}$: 114° C.–115° C.). Yield: 45 g (36%).

(b) 1-(4-methoxy-2,2-diphenylbenzo[1,3]dioxol-5-yl)-2-(1-methylcyclopentylamino)ethanone 35 g of α-bromo-2-methoxy-3,4-diphenylmethylenedioxyacetophenone is refluxed for 1 hour with 45 g of 1-methylcyclopentylamine in 150 mL of ethanol. The solvent is distilled off under reduced pressure, the residue is dissolved in diethyl ether, extracted with water, and the solvent is distilled off under reduced pressure. The residue remaining is dissolved in acetonitrile, acidified with hydrochloric acid, and the crystals obtained are isolated. Yield: 19 g (48%; hydrochloride); melting point: 173° C. (decomposition).

(c) 1-(3,4-dihydroxy-2-methoxyphenyl)-2-(1-methylcyclopentylamino)ethanone 19 g of 1-(4-methoxy-2,2-diphenylbenzo[1,3]dioxol-5-yl)-2-(1-methylcyclopentyl-amino)ethone is refluxed in 190 mL of 15% methanolic hydrochloric acid for 2 hours with stirring. The solvent is distilled off under reduced pressure and the residue remaining is dissolved in acetonitrile. The precipitated crystals are washed with diethyl ether. Yield: 11 g (88%; hydrochloride); melting point: 187° C.–189° C. (decomposition).

(d) 4-[1-hydroxy-2-(1-methylcyclopentylamino)ethyl]-3-methoxybenzene-1,2-diol 5 g of 1-(3,4-dihydroxy-2-methoxyphenyl)-2-(1-methylcyclopentylamino)ethanone hydrochloride is hydrogenated with 0.2 g of platinum(IV) oxide in 200 mL methanol. The catalyst is suction filtered and the solvent is distilled off under reduced pressure. The residue remaining is dissolved in ethanol and combined with 5 g of sodium benzoate. The title compound is isolated in the form of its benzoate. Yield: 4.5 g (70.5%; benzoate); melting point: 179° C.–180° C.

EXAMPLE 3

4-{2-[1,1-dimethyl-2-(2,4,6-trimethylphenyl)ethylamino]-1-hydroxyethyl}-3-methoxybenzene-1,2-diol

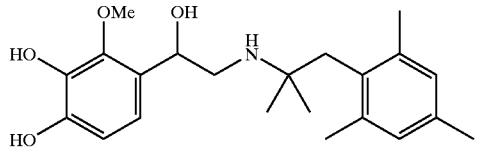

(a) 2-Chloromethyl-1,3,5-trimethylbenzene 400 g of mesitylene is combined with 130 g of paraformaldehyde and 2 L of hydrochloric acid are piped in at 60° C.–70° C. within 7 hours. Then the mixture is extracted with benzene and the organic phase is then washed with 2 N sodium hydroxide solution. The residue is fractionally distilled. Yield: 204 g (36%); $bp_{15}$: 130° C.–140° C.

(b) (2,4,6-trimethylphenyl)acetonitrile 66 g of sodium cyanide is refluxed in 100 mL water and 140 mL of ethanol with stirring, until a clear solution is formed. 136 g of 2-chloromethyl-1,3,5-trimethylbenzene is slowly added dropwise to this solution and the mixture is refluxed for 3 hours with stirring. It is diluted with 1 L of water and extracted three times with 200 mL of benzene. The combined organic phases are washed with water and the solvent is distilled off under reduced pressure. The residue is fractionally distilled. Yield: 92 g (72%); $bp_{15}$: 145° C.–153° C.

(c) (2,4,6-trimethylphenyl)acetic acid 155 g (2,4,6-trimethylphenyl)acetonitrile are added to a solution of 1.1 L of water and 915 mL of concentrated sulfuric acid heated to 50° C. The mixture is refluxed for 6 hours with stirring. Then the reaction mixture is poured onto 3 kg of ice. The solid is suction filtered and washed with water. Yield: 131 g (86%); melting point: 163° C.–166° C.

(d) methyl (2,4,6-trimethylphenyl)acetate 173 g (2,4,6-trimethylphenyl)acetic acid is refluxed in 131 mL of concentrated hydrochloric acid and 1.1 L of methanol for 3 hours with stirring. The solvent is distilled off under reduced pressure and the aqueous phase extracted twice with diethyl ether. The combined organic phases are extracted twice with a saturated aqueous sodium hydrogen carbonate solution and dried with sodium sulfate and the solvent is distilled off under reduced pressure. The residue is fractionally distilled. Yield: 116 g (57%); $bp_{15}$: 140° C.

(e) 2-methyl-1-(2,4,6-trimethylphenyl)propan-2-ol 97 g (79%) of the title compound is prepared from 38 g of magnesium and 222 g of methyl iodide in 1.2 L of diethyl ether and 116 g of methyl (2,4,6-trimethylphenyl)acetate under standard conditions in a Grignard reaction. $bp_{15}$: 140° C.

(f) N-[1,1-dimethyl-2-(2,4,6-trimethylphenyl)ethyl]formamide 90 mL of glacial acetic acid and 33 g of potassium cyanide are combined while cooling with ice. 90 mL of sulfuric acid and 90 mL of glacial acetic acid are then added dropwise at 20° C. 65 g of 2-methyl-1-(2,4,6-trimethylphenyl)propan-2-ol is slowly added to the solution at constant temperature. After the addition has ended, the mixture is stirred for a further hour. The mixture is poured onto ice water, neutralized with sodium carbonate solution, and extracted with diethyl ether. The solvent is distilled off under reduced pressure and the residue is fractionally distilled. Yield: 55 g (74%); $bp_{0.1}$: 155° C.

(g) 1,1-dimethyl-2-(2,4,6-trimethylphenyl)ethylamine 61 g of N-[1,1-dimethyl-2-(2,4,6-trimethylphenyl)ethyl] formamide is refluxed with 35 g of potassium hydroxide in 155 mL ethylene glycol for 9 hours with stirring and, after the reaction has ended, the mixture is poured onto 1 kg of ice. The aqueous phase is extracted three times with diethyl ether and the solvent is distilled off under reduced pressure. The residue is fractionally distilled. Yield: 48 g (89%); bp$_{15}$: 135° C.–140° C.

(h) 2-[1,1-dimethyl-2-(2,4,6-trimethylphenyl)ethylamino]-1-(4-methoxy-2,2-diphenylbenzo[1,3]dioxol-5yl)ethone.

42.5 g of α-bromo-2-methoxy-3,4-diphenylmethylenedioxyacetophenone is refluxed with 22 g of 1,1-dimethyl-2-(2,4,6-trimethylphenyl)ethylamine and 17 g of potassium carbonate in 150 mL of ethanol and 50 mL of acetonitrile for 3 hours with stirring. The solids are filtered off and the solvent is distilled off under reduced pressure. The residue is dissolved in a little acetonitrile and combined with ethereal hydrochloric acid. The crystals precipitated are suction filtered and washed with acetonitrile and ethyl acetate. Yield: 25 g (44%; hydrochloride); melting point: 240° C.–250° C.

(i) 1-(3,4-dihydroxy-2-methoxyphenyl)-2-[1,1-dimethyl-2-(2,4,6-trimethylphenyl)ethylamino]ethanone 17 g of 2-[1,1-dimethyl-2-(2,4,6-trimethylphenyl) ethylamino]-1-(4-methoxy-2,2-diphenylbenzol[1,3]dioxol-5-yl)ethanone hydrochloride is refluxed with 170 mL of 15% methanolic hydrochloric acid for 90 minutes with stirring. The solvent is largely distilled off under reduced pressure. The residue remaining crystallizes out. The crystals are filtered off and washed with diethyl ether. Yield: 10 g (80%; hydrochloride) melting point: 199° C.–201° C.

(j) 4-{2-[1,1-dimethyl-2-(2,4,6-trimethylphenyl) ethylamino]-1-hydroxyethyl}-3-methoxybenzene-1,2-diol 9 g of 1-(3,4-dihydroxy-2-methoxyphenyl)-2-[1,1-dimethyl-2-(2,4,6-trimethylphenyl)-ethylamino]ethanone hydrochloride is hydrogenated with 0.4 g of platinum(IV) oxide in 125 mL of methanol. The catalyst is filtered off and the solvent is distilled off under reduced pressure. The residue is dissolved in 50 mL of ethyl acetate and the precipitated crystals are suction filtered and washed with diethyl ether and ethyl acetate. Yield: 6 g (67%, hydrochloride); melting point: 98° C.–105° C.

EXAMPLE 4

4-[2-(1,1-dimethyl-2-phenylethylamino)-1-hydroxyethyl]-3-methoxybenzene-1,2-diol

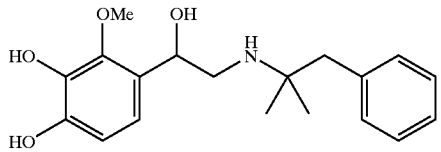

(a) 2-(1,1-dimethylphenylethylamino)-1-(4-methoxy-2,2-diphenylbenzo[1,3]dioxol-5-yl)ethanone 45 g of α-bromo-2-methoxy-3,4-diphenylmethylenedioxyacetophenone is refluxed with 39 g of 1,1-dimethyl-2-phenylethylamine in 200 mL of ethanol for 3 hours. The reaction mixture is acidified with concentrated hydrochloric acid and combined with water. The precipitated crystals are suction filtered and washed successively with water, toluene and ethyl acetate. Yield: 34 g (61%, hydrochloride); melting point: 167° C.–170° C.

(b) 1-(3,4-dihydroxy-2-methoxyphenyl)-2-(1,1-dimethyl-2-phenylethylamino)ethanone 34 g of the HCl salt of 2-(1,1-dimethyl-2-phenylethylamino)-1-(4-methoxy-2,2-diphenylbenzo[1,3] dioxol-5-yl)ethanone is refluxed in 340 mL of 15% methanolic hydrochloric acid for 2 hours. Then the solvent is distilled off under reduced pressure and the residue is dissolved in ethyl acetate. The solid precipitated is suction filtered and washed with ethyl acetate and diethyl ether. Yield: 18 g (77%, hydrochloride); melting point: 192° C.–196° C.

(c) 4-{2-[1,1-dimethyl-2-phenylethylamino]-1-hydroxyethyl}-3-methoxybenzene-1,2-diol 10 g of 1-(3,4-dihydroxy-2-methoxyphenyl)-2-(1,1-dimethyl-2-phenylethylamino)ethanone hydrochloride is hydrogenated with 0.5 g of platinum(IV) oxide in 200 mL methanol. The catalyst is suction filtered and the solvent is distilled off under reduced pressure. The residue remaining is dissolved in 200 mL acetonitrile, combined with 5 g of sodium benzoate and refluxed for 15 minutes. After the excess sodium benzoate has been filtered off, the product which crystallizes out of the filtrate is filtered off and washed with acetonitrile and diethyl ether. Yield: 64.5% (benzoate); melting point: 149° C.–150° C.

EXAMPLE 5

4-{2-[1,1-dimethyl-2-(2,3,5,6-tetramethylphenyl) ethylamino]-1-hydroxyethyl}-3-methoxybenzene-1,2-diol

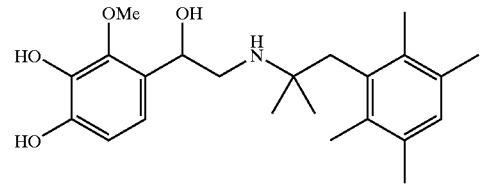

(a) 2-[1,1-dimethyl-2-(2,3,5,6-tetramethylphenyl) ethylamine]-1-(4-methoxy-2,2-diphenylbenzo[1,3]dioxol-5-yl)ethanone 28.5 g of α-bromo-2-methoxy-3,4-diphenylmethylenedioxyacetophenone, 11 g of 1,1-dimethyl-2-(2,3,5,6-tetramethylphenyl)ethylamine, and 8 g of sodium carbonate are refluxed for 3 hours in a solution of 100 mL of ethanol and 10 mL of acetonitrile. Then the inorganic salts are filtered off and the solvent is distilled off. The residue is dissolved in ethyl acetate, acidified with ethereal hydrochloric acid, and combined with diethyl ether. The solid precipitated is filtered off, washed with diethyl ether, and then boiled in water. The product is obtained after filtering and drying. Yield 11 g (hydrochloride); melting point: 194° C.–198° C.

(b) Preparation of 1-(3,4-dihydroxy-2-methoxyphenyl)-2-[1,1-dimethyl-2-(2,3,5,6-tetramethylphenyl)ethylamine] ethanone 11 g of 2-[1,1-dimethyl-2-(2,3,5,6-tetramethylphenyl) ethylamine]-1-(4-methoxy-2,2-diphenylbenzol[1,3]dioxol-5-yl)ethanone hydrochloride is refluxed for 1.5 hours in 110 mL of 15% methanolic hydrochloric acid. The crude product is suction filtered, washed with acetonitrile, and then precipitated from methanol/diethyl ether. Yield: 7 g (hydrochloride); melting point: 213° C.–215° (decomposition).

(c) Preparation of 4-{2-[1,1-dimethyl-2-(2,3,5,6-tetramethylphenyl)ethylamino]-1-hydroxyethyl}-3-methoxybenzene-1,2-diol 7 g of 1-(3,4-dihydroxy-2-methoxyphenyl)-2-[1,1-dimethyl-2-(2,3,5,6-tetramethylphenyl)-ethylamine]

ethanone hydrochloride are hydrogenated with 0.2 g of platinum(IV) oxide in 100 mL of methanol. Then the catalyst is filtered off and the solvent is distilled off. The residue is dissolved in 20 mL water and combined with 1 N hydrochloric acid. The crystals precipitated on cooling are filtered off, washed with ice water, and, after drying, recrystallized from ethyl acetate. Yield: 5 g; melting point: 165° C.–168° C.

EXAMPLE 6

4-[2-(1,1-dimethyl-2-o-tolylethylamino)-1-hydroxyethyl]-3-methoxybenzene-1,2-diol

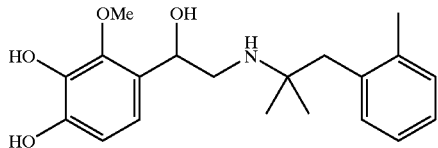

(a) Preparation of 2-(1,1-dimethyl-2-o-tolylethylamine)-1-(4-methoxy-2,2-diphenylbenzo[1,3]dioxol-5-yl)ethanone 26 g of α-bromo-2-methoxy-3,4-diphenylmethylenedioxyacetophenone, 10 g of 1,1-dimethyl-2-o-tolylethylamine, and 9.5 g of sodium carbonate are refluxed for 3 hours in acetonitrile. The inorganic salts are filtered off and the solvent is distilled off. The residue is dissolved in ethyl acetate and acidified with ethereal hydrochloric acid, whereupon the starting amine is precipitated and suction filtered. After the addition of diethyl ether to the filtrate, the product crystallizes out. Yield: 10 g (30%; hydrochloride); melting point: 180° C.–184° C.

(b) Preparation of 1-(3,4-dihydroxy-2-methoxyphenyl)-2-(1,1-dimethyl-2-o-tolylethylamine)ethanone 10 g of 2-(1,1-dimethyl-2-o-tolylethylamine)-1-(4-methoxy-2,2-diphenylbenzo[1,3]dioxol-5-yl)ethanone hydrochloride is refluxed in 100 mL of 15% methanolic hydrochloric acid for 1.5 hours. The reaction mixture is evaporated down and the residue is recrystallized from ethyl acetate. The solid obtained after filtration is washed with diethyl ether. Yield: 6 g (85%; hydrochloride); melting point: 198° C.–201° C. (decomposition).

(c) Preparation of 4-[2-(1,1-dimethyl-2-o-tolylethylamino)-1-hydroxyethyl]-3-methoxybenzene-1,2-diol 4 g of 1-(3,4-dihydroxy-2-methoxyphenyl)-2-(1,1-dimethyl-2-o-tolylethylamine)ethanone hydrochloride is hydrogenated with 0.2 g of platinum(IV) oxide in 50 mL of methanol under normal conditions. Then the catalyst is filtered off and the solvent is distilled off. The residue is combined with 100 mL of acetonitrile and 3 g of sodium benzoate. It is refluxed for 20 minutes and the inorganic matter is filtered off. The product which crystallizes out of the filtrate is suction filtered and recrystallized from acetonitrile. Yield: 2.4 g (benzoate); melting point: 114° C.

It has been found that the compounds of general formula 1are characterized by their versatility of use in the therapeutic field. Particular mention should be made of those applications for which the compounds of formula 1according to the invention are preferably used by virtue of their pharmaceutical effectiveness as betamimetics.

These include, for example, the treatment of asthma, chronic obstructive pulmonary disease (COPD), the inhibition of premature labor in midwifery (tocolysis), the restoration of sinus rhythm in the heart in atrio-ventricular block, as well as the elimination of bradycardic heart rhythm disorders (antiarrhythmic), the treatment of cardiovascular shock (vasodilatation and increasing the cardiac output), as well as the treatment of itching and irritations of the skin.

The compounds of general formula 1may be used on their own or in conjunction with other active substances of formula 1. The compounds of general formula 1may also be used in combination with other pharmacologically active substances. These may be, in particular, anticholinergics, antiallergics, PAF antagonists, PDE-IV inhibitors, leukotriene antagonists, p38 kinase inhibitors, EGFR kinase inhibitors, and corticosteroids as well as combinations of active substances thereof.

Examples of preferred anticholinergics which may be used in conjunction with the compounds of formula 1are compounds selected from among the tiotropium salts, ipratropium salts, oxitropium salts, salts of the compounds known from WO 02/32899: tropenol N-methyl-2,2-diphenylpropionate, scopine N-methyl-2,2-diphenylpropionate, scopine N-methyl-2-fluoro-2,2-diphenylacetate and tropenol N-methyl-2-fluoro-2,2-diphenylacetate; as well as salts of the compounds known from WO 02/32898: tropenol N-methyl-3,3',4,4'-tetrafluorobenzilate, scopine N-methyl-3,3',4,4'-tetrafluorobenzilate, scopine N-methyl-4,4'-dichlorobenzilate, scopine N-methyl-4,4'-difluorobenzilate, tropenol N-methyl-3,3'-difluorobenzilate, scopine N-methyl-3,3'-difluorobenzilate, and tropenol N-ethyl-4,4'-difluorobenzilate, optionally in the form of their hydrates and solvates. By salts are meant those compounds which contain, in addition to the abovementioned cations, as counter-ion, an anion with a single negative charge selected from among the chloride, bromide, and methanesulfonate.

Particularly preferably the active substances within the scope of the present invention are the bromides or methanesulfonates of the abovementioned structures.

Of exceptional interest within the scope of the present invention are, for example, the anticholinergics tiotropium bromide, ipratropium bromide, oxitropium bromide, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide; scopine 4,4'-dichlorobenzilate methobromide, scopine 4,4'-difluorobenzilate methobromide, tropenol 3,3'-difluorobenzilate methobromide, scopine 3,3'-difluorobenzilate methobromide, and tropenol 4,4'-difluorobenzilate ethylbromide, while tiotropium bromide, ipratropium bromide, tropenol 2,2-diphenylpropionate methobromide, scopine 2,2-diphenylpropionate methobromide, scopine 2-fluoro-2,2-diphenylacetate methobromide, and tropenol 2-fluoro-2,2-diphenylacetate methobromide are particularly important.

Drug combinations which contain tiotropium bromide as another active substance in addition to the compounds of formula 1according to the invention are particularly preferred according to the invention. This combination is particularly important for the treatment of asthma or COPD, particularly COPD. Of outstanding importance are particularly those combinations which contain tiotropium bromide in the form of its crystalline monohydrate known from WO 02/30928 or in the form of its crystalline anhydrate known from WO 03/000265.

Within the scope of the present invention, the corticosteroids which may optionally be used in conjunction with the compounds of formula 1may be compounds selected from among flunisolide, beclomethasone, triamcinolone, budesonide, fluticasone, mometasone, ciclesonide, rofleponide, GW 215864, KSR 592, ST-126, and dexamethasone. Preferably, within the scope of the present invention, the corticosteroids are selected from among flunisolide, beclomethasone, triamcinolone, budesonide, fluticasone, mometasone, ciclesonide, and dexamethasone, while budesonide, fluticasone, mometasone, and ciclesonide are important and budesonide and fluticasone are particularly important. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates, or furoates. In some cases, the corticosteroids may also occur in the form of their hydrates.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A, Z-15370, and AWD-12-281. Preferred PDE-IV inhibitors are selected from among enprofylline, roflumilast, ariflo, Z15370, and AWD-12-281, while AWD-12-281 is particularly preferred as the combination partner with the compound of formula 1 according to the invention. Any reference to the abovementioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, according to the invention, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, or maleic acid. According to the invention, the salts selected from among the acetate, hydrochloride, hydrobromide, sulfate, phosphate, and methanesulfonate are preferred in this context.

Within the scope of the present invention, the term dopamine agonists, which may optionally be used in conjunction with the compounds of formula 1, denotes compounds selected from among bromocriptine, cabergolin, α-dihydroergocryptine, lisuride, pergolide, pramipexol, roxindole, ropinirole, talipexole, terguride, and viozan. It is preferable within the scope of the present invention to use, as combination partners with the compounds of formula 1, dopamine agonists selected from among pramipexol, talipexole, and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of antiallergic agents which may be used according to the invention as a combination with the compounds of formula 1 include epinastine, cetirizine, azelastine, fexofenadine, levocabastine, loratadine, mizolastine, ketotifene, emedastine, dimetindene, clemastine, bamipine, hexachloropheniramine, pheniramine, doxylamine, chlorophenoxamine, dimenhydrinate, diphenhydramine, promethazine, ebastine, desloratadine, and meclizine. Preferred antiallergic agents which may be used within the scope of the present invention in combination with the compounds of formula 1 according to the invention are selected from among epinastine, cetirizine, azelastine, fexofenadine, levocabastine, loratadine, ebastine, desloratadine, and mizolastine, epinastine, and desloratadine being particularly preferred. Any reference to the abovementioned antiallergic agents also includes, within the scope of the present invention, a reference to any pharmacologically acceptable acid addition salts thereof which may exist.

Examples of PAF antagonists which may be used according to the invention as a combination with the compounds of formula 1 include 4-(2-chlorophenyl)-9-methyl-2-[3-(4-morpholinyl)-3-propanon-1-yl]-6H-thieno[3,2-f][1,2,4]triazolo[4,3-α][1,4]diazepine and 6-(2-chlorophenyl)-8,9-dihydro-1-methyl-8-[(4-morpholinyl)carbonyl]-4H,7H-cyclopenta[4.5]thieno[3,2-f][1,2,4]triazolo[4,3-a][1,4]diazepine.

Examples of EGFR kinase inhibitors which may be used as a combination with the compounds of formula 1 according to the invention include, in particular, 4-[(3-chloro-4-fluorophenyl)amino]-7-(2-{4-[(S)-(2-oxotetrahydrofuran-5-yl)carbonyl]piperazin-1-yl}-ethoxy)-6-[(vinylcarbonyl)amino]quinazoline, 4-[(3-chloro4-fluorophenyl)amino]-7-[4-((S)-6-methyl-2-oxomorpholin-4-yl)butyloxy]-6-[(vinylcarbonyl)amino]quinazoline, 4-[(3-chloro4-fluorophenyl)amino]-7-[4-((R)-6-methyl-2-oxomorpholin-4-yl)butyloxy]-6-[(vinylcarbonyl)amino]quinazoline, 4-[(3-chloro-4-fluorophenyl)amino]-7-[2-((S)-6-methyl-2-oxomorpholin-4-yl)ethoxy]-6-[(vinylcarbonyl)amino]quinazoline, 4-[(3-chloro-4-fluorophenyl)amino]-6-[(4-{N-[2-(ethoxycarbonyl)ethyl]-N-[(ethoxycarbonyl)methyl]-amino}-1-oxo-2-buten-1-yl)amino]-7-cyclopropylmethoxy-quinazoline, 4-[(R)-(1-phenylethyl)amino]-6-{[4-(morpholin-4-yl)-1-oxo-2-buten-1-yl]amino}-7-cyclopropyl-methoxyquinazoline, and 4-[(3-chloro-4-fluorophenyl)amino]-6-[3-(morpholin-4-yl)propyloxy]-7-methoxyquinazoline. Any reference to the abovementioned EGFR kinase inhibitors also includes, within the scope of the present invention, a reference to any pharmacologically acceptable acid addition salts thereof which may exist. By the physiologically or pharmacologically acceptable acid addition salts thereof which may be formed by the EGFR kinase inhibitors are meant, according to the invention, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, or maleic acid. The salts of the EGFR kinase inhibitors selected from among the salts of acetic acid, hydrochloric acid, hydrobromic acid, sulfuric acid, phosphoric acid, and methanesulfonic acid are preferred according to the invention.

Particularly preferred examples of p38 kinase inhibitors which may be used as a combination with the compounds of formula 1 according to the invention include 1-[5-tert-butyl-2-p-tolyl-2H-pyrazol-3-yl]-3-[4-(2-morpholin-4-yletoxy)naphthalen-1-yl]urea; 1-[5-tert-butyl-2-p-tolyl-2H-pyrazol-3-yl]-3-[4-(2-(1-oxothiomorpholin-4-yl)ethoxy)naphthalen-1-yl]urea; 1-[5-tert-butyl-2-(2-methylpyridin-5-yl)-2H-pyrazol-3-yl]-3-[4-(2-pyridin-4-ylethoxy)naphthalen-1-yl]urea; 1-[5-tert-butyl-2-(2-methoxypyridin-5-yl)-2H- pyrazol-3-yl]-3-[4-(2-morpholin-4-ylethoxy)naphthalen-1-yl]urea; and 1-[5-tert-butyl-2-methyl-2H-pyrazol-3-yl]-3-[4-(2-morpholin-4-ylethoxy)naphthalen-1-yl]urea. Any reference to the abovementioned p38 kinase inhibitors also includes, within the scope of the present invention, a reference to any pharmacologically acceptable acid addition salts thereof which may exist. By the physiologically or pharmacologically acceptable acid addition salts thereof which may be formed by the p38 kinase inhibitors are meant, according to the invention, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

If the compounds of formula 1are used in conjunction with other active substances, the combination with steroids, PDE-IV inhibitors or anticholinergics is particularly preferred, of the categories of compounds mentioned above. The combination with anticholinergics is of particular importance.

Suitable preparations for administering the compounds of formula 1include for example tablets, capsules, suppositories and solutions, etc. Administration of the compounds according to the invention by inhalation is of particular importance according to the invention (particularly for treating asthma or COPD). The content of the pharmaceutically active compound(s) should be in the range from 0.05 wt.-% to 90 wt.-%, preferably 0.1 wt.-% to 50 wt.-% of the composition as a whole. Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc, and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities, the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g., with the addition of isotonic agents, preservatives such as p-hydroxybenzoates or stabilizers such as alkali metal salts of ethylenediaminetetraacetic acid, optionally using emulsifiers and/or dispersants, while if water is used as diluent, for example, organic solvents may optionally be used as solubilizers or dissolving aids, and the solutions may be transferred into injection vials or ampoules or infusion bottles.

Capsules containing one or more active substances or combinations of active substances may, for example, be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as e.g., natural mineral powders (e.g., kaolins, clays, talc, or chalk), synthetic mineral powders (e.g., highly dispersed silicic acid and silicates), sugars (e.g., cane sugar, lactose, and glucose), emulsifiers (e.g., lignin, spent sulfite liquors, methylcellulose, starch, and polyvinylpyrrolidone) and lubricants (e.g., magnesium stearate, talc, stearic acid, and sodium lauryl sulfate).

For oral use, the tablets may obviously contain, in addition to the carriers specified, additives such as sodium citrate, calcium carbonate, and dicalcium phosphate together with various additional substances such as starch, preferably potato starch, gelatine, and the like. Lubricants such as magnesium stearate, sodium lauryl sulfate, and talc may also be used to produce the tablets. In the case of aqueous suspensions, the active substances may be combined with various flavor enhancers or colorings in addition to the abovementioned excipients.

In the preferred use of the compounds of formula 1for the treatment of asthma or COPD, it is particularly preferred according to the invention to use preparations or pharmaceutical formulations which are suitable for inhalation. Inhalable preparations include inhalable powders, propellant-containing metering aerosols, or propellant-free inhalable solutions Within the scope of the present invention, the term propellant-free inhalable solutions also includes concentrates or sterile ready-to-use inhalable solutions. The formulations which may be used within the scope of the present invention are described in more detail in the next part of the specification The inhalable powders which may be used according to the invention may contain 1 either on their own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, or maltose), oligo- and polysaccharides (e.g., dextrans), polyalcohols (e.g., sorbitol, mannitol, or xylitol), salts (e.g., sodium chloride or calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 $\mu$m, preferably between 10 $\mu$m and 150 $\mu$m, most preferably between 15 $\mu$m and 80 $\mu$m. In some cases it may seem appropriate to add finer excipient fractions with an average particle size of 1 $\mu$m to 9 $\mu$m to the excipient mentioned above. These finer excipients are also selected from the group of possible excipients listed hereinbefore. Finally, in order to prepare the inhalable powders according to the invention, micronised active substance 1, preferably with an average particle size of 0.5 $\mu$m to 10 $\mu$m, more preferably from 1 $\mu$m to 5 $\mu$m, is added to the excipient mixture. Processes for producing the inhalable powders according to the invention by grinding and micronizing and finally mixing the ingredients together are known from the prior art. The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane, or isobutane and halohydrocarbons such as halogenated alkane derivatives selected from TG134a and TG227 and mixtures thereof.

The propellant-driven inhalation aerosols may also contain other ingredients such as cosolvents, stabilizers, surfactants, antioxidants, lubricants, and pH adjusters. All these ingredients are known in the art.

The propellant-driven inhalation aerosols according to the invention mentioned above may be administered using inhalers, such as metered dose inhalers (MDI), known in the art.

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid etc. Preferred inorganic acids are hydrochloric and sulfuric acids. It is also possible to use the acids which have already formed an acid addition salt with one of the active substances. Of the organic acids, ascorbic acid, fumaric acid, and citric acid are preferred. If desired, mixtures of the above acids may be used, particularly in the case of acids which have other properties in addition to their acidifying qualities, e.g., as flavorings, antioxidants or complexing agents, such as citric acid or ascorbic acid, for example. According to the invention, it is particularly preferred to use hydrochloric acid to adjust the pH.

If desired, the addition of edetic acid (EDTA) or one of the known salts thereof, sodium edetate, as stabilizer or complexing agent is unnecessary in these formulations. Other embodiments may contain this compound or these compounds. In a preferred embodiment the content based on sodium edetate is less than 100 mg/100 mL, preferably less than 50 mg/100 mL, more preferably less than 20 mg/100 mL. Generally, inhalable solutions in which the content of sodium edetate is from 0 to 10 mg/100 mL are preferred.

Cosolvents and/or other excipients may be added to the propellant-free inhalable solutions. Preferred cosolvents are those which contain hydroxyl groups or other polar groups, e.g., alcohols, particularly isopropyl alcohol, glycols, particularly propyleneglycol, polyethyleneglycol, polypropyleneglycol, glycol ether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants and/or preservatives which guarantee or prolong the shelf life of the finished pharmaceutical formulation, flavorings, vitamins, and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art. The preservatives mentioned above are preferably present in concentrations of up to 50 mg/100 mL, more preferably between 5 and 20 mg/100 mL.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterized by a high potency even at doses in the µg range. The compounds of formula 1 may also be used effectively above the µg range. The dosage may then be in the gram range, for example.

Particularly when administered by routes other than by inhalation the compounds according to the invention may be administered in higher doses (for example, but not restrictively, in the range from 1 mg to 1000 mg).

The following examples of formulations illustrate the present invention without restricting its scope.

Examples of Pharmaceutical Formulations

| A. Tablet | |
| --- | --- |
| Ingredient | Amount (mg) |
| active substance | 100 |
| lactose | 140 |
| maize starch | 240 |
| polyvinylpyrrolidone | 15 |
| magnesium stearate | 5 |
| Total | 500 |

The finely ground active substance, lactose, and some of the maize starch are mixed together. The mixture is screened, then moistened with a solution of polyvinylpyrrolidone in water, kneaded, wet granulated and dried. The granules, the remaining maize starch, and the magnesium stearate are screened and mixed together. The mixture is pressed into tablets of suitable shape and size.

| B. Tablet | |
|---|---|
| Ingredient | Amount (mg) |
| active substance | 80 |
| maize starch | 190 |
| microcrystalline cellulose | 35 |
| polyvinylpyrrolidone | 15 |
| sodium-carboxymethyl starch | 23 |
| magnesium stearate | 2 |
| Total | 400 |

The finely ground active substance, some of the maize starch, lactose, microcrystalline cellulose, and polyvinylpyrrolidone are mixed together, the mixture is screened and worked with the remaining maize starch and water to form granules which are dried and screened. To these are added the sodium carboxymethyl starch and the magnesium stearate, they are mixed together, and the mixture is pressed into tablets of suitable size.

| C. Ampoule Solution | |
|---|---|
| Ingredient | Amount |
| active substance | 50 mg |
| sodium chloride | 50 mg |
| water for inj. | 5 mL |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg, and 50 mg of active substance.

| D. Metered Dose Aerosol | |
|---|---|
| Ingredient | Amount |
| active substance | 0.005 |
| sorbitan trioleate | 0.1 |
| monofluorotrichloromethane and TG134a:TG227 (2:1) | to 100 |

The suspension is transferred into a conventional aerosol container with metering valve. Preferably 50 μL suspension are released on each actuation. The active substance may also be released in higher doses if desired (e.g., 0.02 wt.-%).

| E. Solution | |
|---|---|
| Ingredient | Amount (mg/100 mL) |
| tiotropium bromide | 333.3 |
| benzalkonium chloride | 10.0 |
| EDTA | 50.0 |
| HCl (1 N) | to pH 3.4 |

This solution may be prepared in the conventional manner.

| F. Inhalable Powder | |
|---|---|
| Ingredient | Amount |
| tiotropium bromide | 6 μg |
| lactose monohydrate | to 25 mg |

The inhalable powder is prepared in the conventional manner by mixing the individual ingredients.

We claim:

1. A method for treatment of asthma, chronic obstructive pulmonary disease (COPD), premature labor in midwifery (tocolysis), atrioventricular block, bradycardic heart rhythm disorders, cardiovascular shock, or itching and irritation of the skin in a patient, the method comprising administering to the patient in need thereof an effective amount of a compound of general formula 1

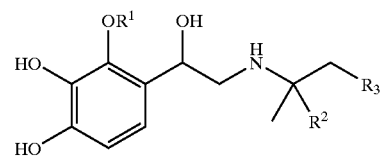

wherein:

$R^1$ is $C_1$–$C_4$-alkyl;

$R^2$ is $C_1$–$C_4$-alkyl; and $R^3$ is $C_1$–$C_4$-alkyl or phenyl, each optionally mono- or polysubstituted, or $R^2$ and $R^3$ together are —CH$_2$—CH$_2$— or —CH$_2$—CH$_2$—CH$_2$—, or the corresponding acid addition salt with a pharmacologically acceptable acid.

2. A pharmaceutical composition comprising:

(a) a compound of formula 1

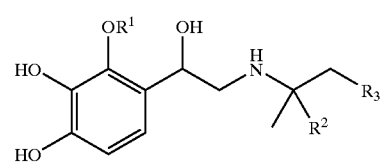

wherein:

$R^1$ is $C_1$–$C_4$-alkyl;

$R^2$ is $C_1$–$C_4$-alkyl; and $R^3$ is $C_1$–$C_4$-alkyl or phenyl, each optionally mono- or polysubstituted, or $R^2$ and $R^3$ together are —CH$_2$—CH$_2$— or —CH$_2$—CH$_2$—CH$_2$—, or the corresponding acid addition salt with a pharmacologically acceptable acid; and (b) at least one other active substance selected from anticholinergics, antiallergics, PAF antagonists, PDE-IV inhibitors, leukotriene antagonists, p38 kinase inhibitors, EGFR kinase inhibitors, and corticosteroids.

3. The pharmaceutical composition of claim 2, further comprising a physiologically acceptable excipient.

4. A pharmaceutical composition comprising:
(a) a compound of formula 1

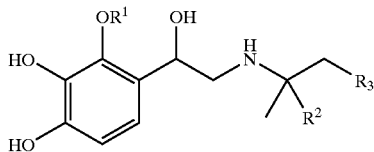

wherein:
R$^1$ is C$_1$–C$_4$-alkyl;
R$^2$ is C$_1$–C$_4$-alkyl; and
R$^3$ is C$_1$–C$_4$-alkyl or phenyl, each optionally mono- or polysubstituted, or R$^1$ and R$^3$ together are —CH$_2$—CH$_2$— or —CH$_2$—CH$_2$—CH$_2$—,
or the corresponding acid addition salt with a pharmacologically acceptable acid; and
(b) tiotropium bromide.

5. The pharmaceutical composition of claim 4, further comprising a physiologically acceptable excipient.

6. A pharmaceutical composition comprising:
(a) a compound of formula 1

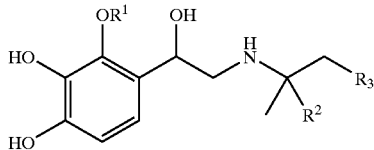

wherein:
R$^1$ is C$_1$–C$_4$-alkyl;
R$^2$ is C$_1$–C$_4$-alkyl; and
R$^3$ is C$_1$–C$_4$-alkyl or phenyl, each optionally mono- or polysubstituted, or R$^2$ and R$^3$ together are —CH$_2$—CH$_2$— or —CH$_2$—CH$_2$—CH$_2$—,
or the corresponding acid addition salt with a pharmacologically acceptable acid;
(b) tiotropium bromide; and
(c) at least one other active substance selected from anticholinergics, antiallergics, PAF antagonists, PDE-IV inhibitors, leukotriene antagonists, p38 kinase inhibitors, EGFR kinase inhibitors, and corticosteroids.

7. The pharmaceutical composition of claim 6, further comprising a physiologically acceptable excipient.

8. The method according to claim 1, comprising administering to the patient in need thereof an effective amount of the compound of general formula 1

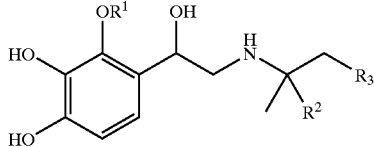

wherein:
R$^3$ is C$_1$–C$_4$-alkyl or phenyl, each optionally mono-, di-, tri-, or tetrasubstituted by one or more groups selected from C$_1$–C$_3$-alkyl, CF$_3$, methoxy, ethoxy, hydroxy, fluorine, chlorine, bromine, —OCF$_3$, —CHF$_2$, and —NHCOCH$_3$, and —NHSO$_2$CH$_3$, or R$^2$ and R$^3$ together are —CH$_2$—CH$_2$— or —CH$_2$—CH$_2$—CH$_2$—,
or the corresponding acid addition salt with a pharmacologically accetable acid.

9. A method according to claim 1 comprising administering to the patient in need thereof an effective amount of the compound of general formula 1

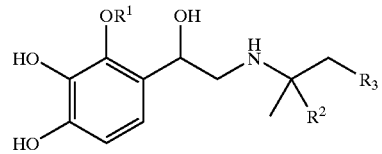

wherein:
R$^3$ is C$_1$–C$_4$-alkyl or phenyl, each optionally mono-, di-, tri-, or tetrasubstituted by one or more groups selected from methyl, ethyl, CF$_3$, methoxy, ethoxy, and hydroxy, or R$^2$ and R$^3$ together are —CH$_2$—CH$_2$— or —CH$_2$—CH$_2$—CH$_2$—,
or the corresponding acid addition salt with a pharmacologically acceptable acid.

10. A method according to claim 1 comprising administering to the patient in need thereof an effective amount of the compound of general formula 1

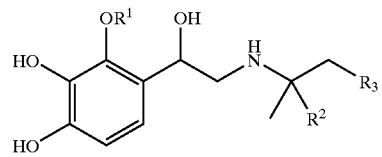

wherein:
R$^3$ is C$_1$–C$_4$-alkyl or phenyl, each optionally mono-, di-, tri-, or tetrasubstituted by one or more groups selected from methyl, CF$_3$, methoxy, and hydroxy, or R$^2$ and R$^3$ together are —CH$_2$—CH$_2$—,
or the corresponding acid addition salt with a pharmacologically accevtable acid.

11. A method according to claim 1 comprising administering to the patient in need thereof an effective amount of the compound of general formula 1

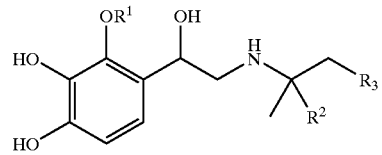

wherein:
R$^1$ is methyl or ethyl;
R$^2$ is methyl; and
R$^3$ is methyl, ethyl, or phenyl, each optionally mono-, di-, tri-, or tetrasubstituted by one or more groups selected from methyl, CF$_3$, methoxy, and hydroxy, or R$^2$ and R$^3$ together are —CH$_2$—CH$_2$—,
or the corresponding acid addition salt with a pharmacologically acceptable acid.

12. A method according to claim 1 comprising administering to the patient in need thereof an effective amount of the compound of general formula 1

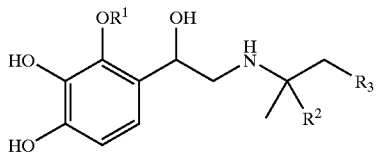

wherein:
$R^1$ is methyl;
$R^2$ is methyl; and
$R^3$ is methyl or phenyl, each optionally mono-, di-, or trisubstituted by one or more groups selected from methyl, ethyl, and hydroxy, or $R^2$ and $R^3$ together are —CH$_2$—CH$_2$—,
or the corresponding acid addition salt with a pharmacologically acceptable acid.

13. A method according to claim 1 comprising administering to the patient in need thereof an effective amount of the compound of general formula 1

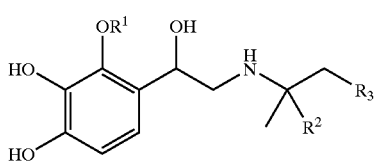

wherein:
$R^1$ is methyl;
$R^2$ is methyl; and
$R^3$ is methyl or phenyl, or $R^2$ and $R^3$ together are —CH$_2$—CH$_2$—,
or the corresponding acid addition salt with a pharmacologically acceptable acid.

14. The pharmaceutical composition according to claim 2, comprising the compound of general formula 1

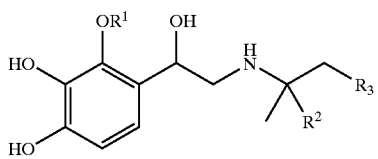

wherein:
$R^3$ is $C_1$–$C_4$-alkyl or phenyl, each optionally mono-, di-, tri-, or tetrasubstituted by one or more groups selected from $C_1$–$C_3$-alkyl, CF$_2$, methoxy, ethoxy, hydroxy, fluorine, chlorine, bromine, —OCF$_3$, —CHF$_3$, —NHCOCH$_3$, and —NHSO$_2$CH$_3$, or $R^2$ and $R^3$ together are —CH$_2$—CH$_2$— or —CH$_2$—CH$_2$—CH$_2$—,
or the corresponding acid addition salt with a pharmacologically acceptable acid.

15. The pharmaceutical composition according to claim 2, comprising the compound of general formula 1

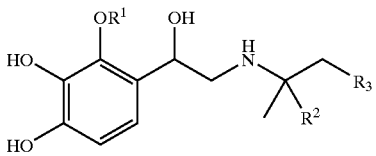

wherein:
$R^3$ is $C_1$–$C_4$-alkyl or phenyl, each optionally mono-, di-, tri-, or tetrasubstituted by one or more groups selected from methyl, ethyl, CF$_3$, methoxy, ethoxy, and hydroxy, or $R^2$ and $R^3$ together are —CH$_2$—CH$_2$— or —CH$_2$—CH$_2$—CH$_2$—,
or the corresponding acid addition salt with a pharmacologically acceptable acid.

16. The pharmaceutical composition according to claim 2, comprising the compound of general formula 1

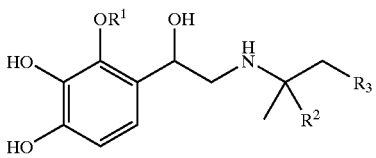

wherein:
$R^3$ is $C_1$-alkyl or phenyl, each optionally mono-, di-, tri-, or tetrasubstituted by one or more groups selected from methyl, CF$_3$, methoxy, and hydroxy, or $R^2$ and $R^3$ together are —CH$_2$—CH$_2$—,
or the corresponding acid addition salt with a pharmacologically acceptable acid.

17. The pharmaceutical composition accordina to claim 2, comprising the compound of general formula 1

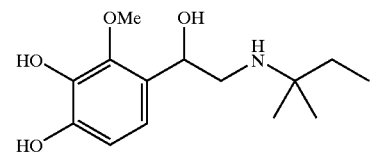

wherein:
$R^1$ is methyl or ethyl;
$R^2$ is methyl; and
$R^3$ is methyl, ethyl, or phenyl, each optionally mono-, di-, tri-, or tetrasubstituted by one or more arouns selected from methyl, CF$_3$, methoxy, and hydroxy, or $R^2$ and $R^3$ together are —CH$_2$—CH$_2$—,
or the corresponding acid addition salt with a pharmacologically acceptable acid.

18. The pharmaceutical composition according to claim 2, comprising the compound of general formula 1

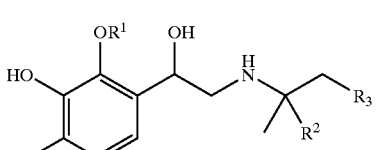

wherein:
$R^1$ is methyl;
$R^2$ is methyl; and

R³ is methyl or phenyl, each optionally mono-, di-, or trisubstituted by one or more groups selected from methyl, ethyl, and hydroxy, or R² and R³ together are —CH₂—CH₂—, or the corresponding acid addition salt with a pharmacologically acceptable acid.

19. The pharmaceutical composition according to claim 2, comprising the comnound of general formula 1

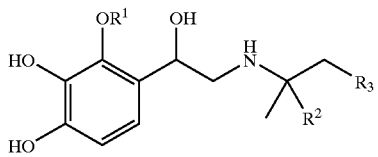
1 wherein:

R¹ is methyl;

R² is methyl; and

R³ is methyl or phenyl, or R² and R³ together are —CH₂—CH₂—, or the corresponding acid addition salt with a pharmacologically acceptable acid.

20. The pharmaceutical composition according to claim 4, comprising the compound of general formula 1

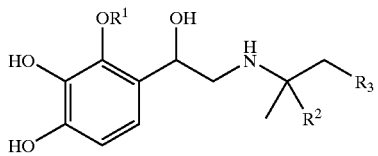
1 wherein:

R³ is C₁–C₄-alkyl or phenyl, each optionally mono-, di-, tri-, or tetrasubstituted by one one or more groups selected from C₁–C₄-alkyl, CF₃, methoxy, ethoxy, hydroxy, fluorine, chlorine, bromine, —OCF₃, —CHF₂, —NHCOCH₃, and —NHSO₂CH₃, or R² and R³ together are —CH₂—CH₂— or —CH₂—CH₂CH₂—, or the corresponding acid addition salt with a pharmacologically accentable acid.

21. The pharmaceutical composition according to claim 4, comprising the comnound of general formula 1

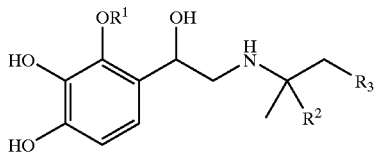
1 wherein:

R³ is C₁–C₄-alkyl or phenyl, each optionally mono-, di-, tri-, or tetrasubstituted by one or more groups selected from methyl, ethyl, CF₃, methoxy, ethoxy, and hydroxy, or R² and R³ together are —CH₂—CH₂— or —CH₂—CH₂—CH₂—, or the corresponding acid addition salt with a pharmacologically acceptable acid.

22. The pharmaceutical composition according to claim 4, comprising the compound of general formula 1

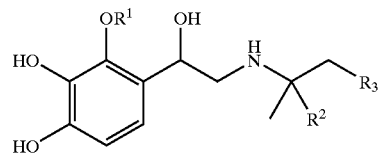
1 wherein:

R³ is C₁–C₄-alkyl or phenyl, each optionally mono-, di-, tri-, or tetrasubstituted by one or more groups selected from methyl, CF₃, methoxy, and hydroxy, or R² and R³ together are —CH₂—CH₂—, or the corresponding acid addition salt with a pharmacologically acceptable acid.

23. The pharmaceutical composition according to claim 4, comprising the compound of general formula 1

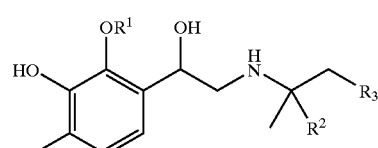
1 wherein:

R¹ is methyl or ethyl;

R² is methyl; and

R³ is methyl, ethyl, or phenyl, each optionally mono-, di-, tri-, or tetrasubstituted by one or more groups selected from methyl, CF₃, methoxy, and hydroxy, or R² and R³ together are —CH₂—CH₂—, or the corresponding acid addition salt with a pharmacologically acceptable acid.

24. The pharmaceutical composition according to claim 4, comprising the compound of general formula 1

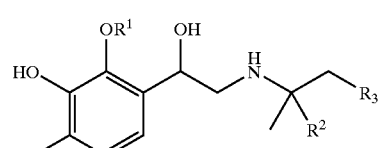
1 wherein:

R¹ is methyl;

R² is methyl; and

R³ is methyl or phenyl, each optionally mono-, di-, or trisubstituted by one or more groups selected from methyl, ethyl, and hydroxy, or R² and R³ together are —CH₂—CH₂—, or the corresponding acid addition salt with a pharmacologically acceotable acid.

25. The pharmaceutical composition according to claim 4, comprising the compound of general formula 1

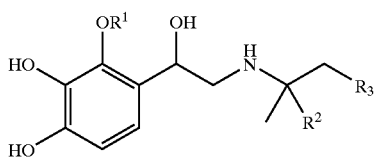

wherein:
- $R^1$ is methyl;
- $R^2$ is methyl; and
- $R^3$ is methyl or phenyly or $R^2$ and $R^3$ together are —CH$_2$—CH$_2$—, or the corresponding acid addition salt with a pharmacologically acceptable acid.

26. The pharmaceutical comnosition according to claim 6, comprising the compound of general formula 1

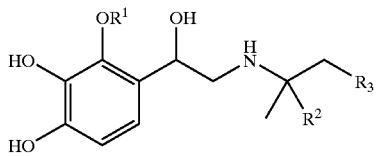

wherein:
- $R^3$ is $C_1$–$C_4$-alkyl or phenyl, each optionally mono-, di-, tri-, or tetrasubstituted by one or more groups selected from $C_1$–$C_3$-alkyl, CF$_3$, methoxy, ethoxy, hydroxy, fluorine, chlorine, bromine, —OCF$_3$, —CHF$_2$, —NHCOCH$_3$, and —NHSO$_2$CH$_3$, or $R^2$ and $R^3$ together are —CH$_2$—CH$_2$— or —CH$_2$—CH$_2$—CH$_2$—, or the corresponding acid addition salt with a pharmacologically acceptable acid.

27. The pharmaceutical composition according to claim 6, comprising the compound of general formula 1

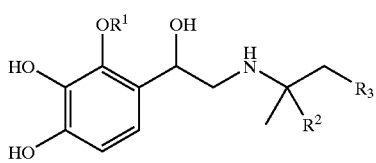

wherein:
- $R^3$ is $C_1$–$C_4$-alkyl or phenyl, each optionally mono-, di-, tri-, or tetrasubstituted by one or more groups selected from methyl, ethyl, CF$_3$, methoxy, ethoxy, and hydroxy, or $R^2$ and $R^3$ together are —CH$_2$—CH$_2$— or —CH$_2$—CH$_2$—CH$_2$—, or the corresponding acid addition salt with a pharmacologically acceptable acid.

28. The pharmaceutical composition according to claim 6, comprising the compound of general formula 1

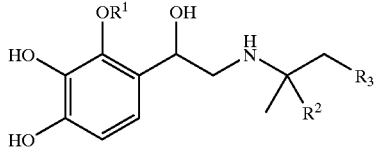

wherein:
- $R^3$ is $C_1$–$C_4$-alkyl or phenyl, each optionally mono-, di-, tri-, or tetrasubstituted by one or more groups selected from methyl, CF$_3$, methoxy, and hydroxy, or $R^2$ and $R^3$ together are —CH$_2$—CH$_2$—, or the corresponding acid addition salt with a pharmacologically acceotable acid.

29. The pharmaceutical composition according to claim 6, comprising the compound of general formula 1

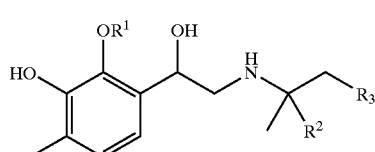

wherein:
- $R^1$ is methyl or ethyl;
- $R^2$ is methyl; and
- $R^3$ is methyl, ethyl, or phenyl, each optionally mono-, di-, tri-, or tetrasubstituted by one or more groups selected from methyl, CF$_3$, methoxy, and hydroxy, or $R^2$ and $R^3$ together are —CH$_2$—CH$_2$—, or the corresponding acid addition salt with a pharmacologically acceptable acid.

30. The pharmaceutical composition according to claim 6, comprising the compound of general formula 1

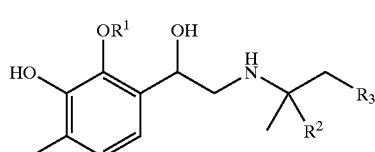

wherein:
- $R^1$ is methyl;
- $R^2$ is methyl; and
- $R^3$ is methyl or phenyl, each optionally mono-, di-, or trisubstituted by one or more groups selected from methyl, ethyl, and hydroxy, or $R^2$ and $R^3$ together are —CH$_2$—CH$_2$—, or the corresponding acid addition salt with a pharmacologically acceptable acid.

31. The pharmaceutical comoosition according to claim 6, comprising the compound of general formula 1

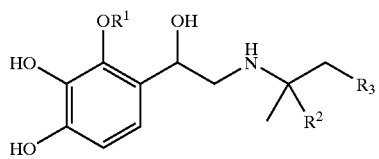

wherein:
- $R^1$ is methyl;
- $R^2$ is methyl; and
- $R^3$ is methyl or phenyl, or $R^2$ and $R^3$ together are —CH$_2$—CH$_2$—, or the corresponding acid addition salt with a pharmacologically acceptable acid.

* * * * *